US008226613B2

(12) United States Patent
Watanabe et al.

(10) Patent No.: US 8,226,613 B2
(45) Date of Patent: Jul. 24, 2012

(54) STYLET AND CATHETER SET

(75) Inventors: Motonori Watanabe, Fukuroi (JP); Nobuatsu Kanie, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 35 days.

(21) Appl. No.: 12/841,205

(22) Filed: Jul. 22, 2010

(65) Prior Publication Data

US 2011/0028904 A1    Feb. 3, 2011

(30) Foreign Application Priority Data

Jul. 30, 2009    (JP) ................................ 2009-177171

(51) Int. Cl.
*A61M 5/178*    (2006.01)

(52) U.S. Cl. .............................. 604/164.01; 604/164.09

(58) Field of Classification Search ............ 604/164.09, 604/164.01, 164.12, 912, 915, 917, 544
See application file for complete search history.

(56) References Cited

U.S. PATENT DOCUMENTS

| | | | |
|---|---|---|---|
| 3,050,066 A * | 8/1962 | Koehn ........................ | 604/97.01 |
| 3,957,055 A * | 5/1976 | Linder et al. ............. | 128/200.26 |
| 5,073,166 A | 12/1991 | Parks et al. | |
| 5,637,097 A | 6/1997 | Yoon | |
| 7,241,308 B2 * | 7/2007 | Andreas et al. .............. | 623/1.11 |
| 2008/0142005 A1 * | 6/2008 | Schnell ..................... | 128/200.26 |
| 2009/0187141 A1 * | 7/2009 | Lareau et al. .................. | 604/43 |

FOREIGN PATENT DOCUMENTS

| | | |
|---|---|---|
| JP | 2008-539917 | 11/2008 |
| WO | WO 98/15309 | 4/1998 |
| WO | WO 02/085225 | 10/2002 |

OTHER PUBLICATIONS

European Search Report from European Application No. EP 10 00 7535 date completed Sep. 28, 2011.

* cited by examiner

*Primary Examiner* — Jackie Ho
*Assistant Examiner* — Weng Lee
(74) *Attorney, Agent, or Firm* — Thomas M. Johnston, Esq.

(57) ABSTRACT

A stylet is provided which makes it possible to improve the handling of a catheter while also facilitating insertion of the catheter. A catheter set having such a stylet is also provided. A stylet with a hole and a stylet without a hole include, respectively: a stylet main body; an engaging part; a film-like linking part for linking the stylet main body and the engaging part; and a soft tip end part which is provided at a tip end of the engaging part. The engaging part has a tapered tubular shape which can expand and contract thanks to an alternating arrangement of soft parts and rigid parts in the peripheral direction. The stylet main body is then pulled rearwards from a state in which the stylet with a hole and the stylet without a hole are assembled with a catheter, thereby enabling the engaging part, which can engage with the edge of the opening of the catheter, to contract in the radial direction and be withdrawn.

6 Claims, 10 Drawing Sheets

STYLET AND CATHETER SET

CROSS-REFERENCE TO RELATED APPLICATIONS

This application claims priority under 35 U.S.C. §119 to Japanese Patent Application Serial No. 2009-177171, filed Jul. 30, 2009, the entire contents of which are incorporated herein by reference in their entirety.

TECHNICAL FIELD

The present invention relates to a stylet which is inserted into a catheter in order to improve the ease of insertion of the catheter, and to a catheter set provided with such a stylet.

DESCRIPTION OF RELATED ART

It is conventional practice for the tube of a catheter or a cannula etc. to be made indwelling within a lumen inside a patient's body, for instance a blood vessel or the trachea, in order to carry out hemodialysis or a treatment to maintain the respiratory tract (see PCT Application JP 2008-539917, for example). This tracheal cannula (catheter) is inserted into the patient's trachea percutaneously using an insertion aid (stylet) and a displacer. That is to say, the insertion aid has a structure in which a cylindrical stem and a conical tip end part are linked by a tubular stem section, and the displacer consists of a rod-like body which can be inserted into the insertion aid. The conical tip end part projects further towards the outer periphery than the outer peripheral surface of the stem, and the rear end surface thereof includes a surface which can engage the tip end surface of the tracheal cannula.

Furthermore, the conical tip end part and the stem section expand when the displacer is inserted therein, and the rear end surface of the conical tip end part engages with the tip end surface of the tracheal cannula. When the displacer is withdrawn, the conical tip end part and the stem section contract so that they can be inserted into the tracheal cannula. Consequently, when the tracheal cannula is inserted into the patient's trachea, the stem is inserted into the tracheal cannula and the conical tip end part projects from the tip end of the tracheal cannula. The displacer is then further inserted from inside the stem into the conical tip end part. This allows the expanded shape of the conical tip end part to be maintained, and therefore the tracheal cannula is easily inserted into the trachea. When the tip end of the tracheal cannula reaches inside the trachea, the displacer is withdrawn, and then the stem and the conical tip end part etc. are also withdrawn, whereby it is possible to leave only the tracheal cannula remaining inside the patient's body.

However, percutaneous insertion of the tracheal cannula described above into a patient's body requires the displacer in addition to the insertion aid, which increases the number of components and hinders the operation. Furthermore, if a multi-lumen catheter is used instead of a tracheal cannula, several displacers as well as several insertion aids are needed.

SUMMARY

The present invention has been devised in view of the situation outlined above, and it aims to provide a stylet which makes it possible to improve handling while also facilitating insertion of the catheter, and to provide a catheter set having such a stylet.

In order to achieve the aim described above, structural features of the stylet according to the present disclosure lie in the fact that it is a stylet which is inserted into a lumen of a catheter, the stylet including: a stylet main body; a tapered tubular engaging part of which a rear end engages with an edge at a tip end opening of the catheter by pressing the engaging part towards a base end of the catheter in a state in which the shape of a tip end part is substantially maintained and a rear part is urged so as to expand in the radial direction and projects from the tip end opening of the catheter; and a soft linking part which links the tip end of the stylet main body and the rear end of the engaging part; whereby when the stylet main body is pulled towards the base end of the catheter, from a state in which the stylet main body is inserted into the lumen of the catheter and the engaging part is projecting from the tip end opening of the catheter, the rear part of the engaging part contracts in the radial direction, and the engaging part passes through the lumen of the catheter so that it can be withdrawn at the base end of the catheter.

The stylet according to the present disclosure includes a long stylet main body, a tapered tubular engaging part, and a soft linking part for linking the stylet main body and the engaging part. When the stylet main body is inserted into the lumen of the catheter with the engaging part projecting from the tip end opening of the catheter so that the stylet is assembled with the catheter, a curved surface having a diameter which steadily grows narrower from the tip end of the catheter towards the front is formed at the tip end of the catheter by means of the tapered engaging part. Furthermore, the tip end opening of the catheter is closed off by means of the engaging part. As a result, the insertion resistance of the catheter is reduced and handling is improved when the catheter is inserted into the body. Furthermore, if a force which presses the engaging part rearwards is applied during the insertion, the rear end of the engaging part engages with the edge at the tip end opening of the catheter, and therefore the engaging part does not retract inside the catheter.

Furthermore, when the tip end of the catheter reaches a specific position inside the body and the stylet is withdrawn from the catheter, the stylet is pulled towards the rear of the catheter (towards the base end). By means of this, the linking part is first pulled by the stylet main body and retracts inside the catheter. Then the rear part of the engaging part is pulled by the linking part towards the rear of the catheter and in a direction which causes radial contraction, and the engaging part contracts as it enters the catheter and is also pulled towards the rear inside the catheter. Consequently, the stylet can be easily withdrawn from the catheter by an operation which simply involves pulling the stylet towards the rear of the catheter.

Moreover, for the linking part according to the present disclosure, use is made of a component which is sufficiently soft and readily deforms and can enter the catheter when the stylet is pulled towards the base end of the catheter. Furthermore, a soft part may also be provided at the tip end of the engaging part in the stylet according to the present disclosure. By virtue of this, the engaging part readily deforms because it can move easily with the tip end at the center when the rear part of the engaging part undergoes radial expansion or contraction. The soft part in this case should be sufficiently soft to be able to deform itself, without hindering deformation of at least the engaging part.

Further structural features of the stylet according to the present disclosure lie in the fact that the engaging part includes rigid parts and soft parts arranged alternately in the peripheral direction in order to allow radial expansion and contraction.

The soft parts and rigid parts in this case extend so as to substantially lie in the front to rear direction (the axial direction of the engaging part). This means that when the stylet main body is pulled and the rear end of the engaging part is urged towards the center in the radial direction, the soft parts are flattened and distorted, bringing the rigid parts closer together so that the whole of the engaging part contracts. Furthermore, when the force which urges the rear end of the engaging part towards the center in the radial direction is released, the soft parts return to their original shape, whereby the rear part of the engaging part is urged in such a way that it expands in the radial direction.

Consequently, when the catheter is inserted into the body, the rear end of the rigid parts of the engaging part engage with the edge at the tip end opening of the catheter, and when the stylet is withdrawn from the catheter, the operation simply involves pulling the stylet main body. It should be noted that the rigid parts are sufficiently rigid that the shape thereof is maintained and the rear end can engage with the edge at the tip end opening of the catheter when these rigid parts are pressed towards the base end of the catheter and they are projecting from the tip end opening of the catheter. The soft parts are sufficiently soft that they readily deform when a force is applied thereto.

Further structural features of the stylet according to the present disclosure lie in the fact that the rear part of the engaging part is formed as a bellows-like expandable shape in order to allow the engaging part to expand and contract in the radial direction. This means that when the catheter is inserted into the body, the engaging part is pressed rearwards, whereby the rear part of the engaging part contracts and the outer diameter of the contracted section increases and engages with the edge at the tip end opening of the catheter. Furthermore, when the stylet is withdrawn from the catheter, the rear part of the engaging part extends, whereby the outer diameter of that portion becomes smaller, and the stylet can be withdrawn from the catheter. In this case, the outer diameter of the front part of the engaging part is made to be smaller than the inner diameter of the catheter.

Further structural features of the stylet according to the present disclosure lie in the fact that the linking part includes an annular film part for linking the peripheral edge at the tip end of the stylet main body and the peripheral edge at the rear end of the engaging part. This means that when the stylet is pulled to withdraw it from the catheter, the force transmitted from the stylet main body to the engaging part is substantially uniform over the whole of the peripheral edge at the rear end of the engaging part, and therefore the stylet can be smoothly withdrawn.

Further structural features of the stylet according to the present disclosure lie in the fact that a through-hole for the passage of a guidewire is provided from the tip end of the engaging part towards the rear end of the stylet main body. This means that the operation to make the catheter indwelling in the patient's body is simplified. Furthermore, the stylet main body is tubular in shape, which means that it is possible to provide the through-hole, and the material used in producing the stylet can be minimized and the stylet can be made more lightweight.

Further structural features of the stylet according to the present disclosure lie in the fact it includes two stylets, and when the two stylets have been inserted into the lumina of the catheter, the two engaging parts projecting from the tip end opening of the catheter form a substantially conical shape. This means that the insertion resistance of the catheter is further reduced and the handling when the catheter is inserted into the body is improved. Furthermore, in this case, a through-hole for the passage of a guidewire is preferably provided from the tip end of the engaging part towards the rear end of the stylet main body in at least one of the two stylets. This means that the operation to make the catheter indwelling in the patient's body can be simplified using the two stylets.

Structural features of the catheter set according to the present disclosure lie in the fact that the catheter has two lumina which are divided by a dividing wall, and any of the stylets described above can be inserted into the two lumina. This means that the stylets can be inserted into the respective lumina of what is known as a double-lumen catheter which has two lumina, and therefore the strength of the catheter is enhanced, which also improves handling. It should be noted that the dividing wall in this case extends in the axial direction of the catheter, in a state in which communication in the two lumina is provided from the rear end of the catheter to the tip end thereof, respectively.

Furthermore, with the catheter set according to the present disclosure, the tip end of the dividing wall projects outside the tip end opening of the catheter, and this projecting section is positioned between the engaging parts of the stylets which are inserted into the two lumina, respectively. The projecting section of the dividing wall in this case is provided to separate the two lumina not only inside the catheter, but also close to the inside part outside the catheter, and even if the dividing wall is provided with this kind of projecting section, the projecting section can be protected as it is positioned between the engaging parts of the two stylets.

Furthermore, with the catheter set according to the present disclosure, the double-lumen catheter is a dialysis catheter which has a blood removal lumen and a blood feed lumen, and a through-hole for the passage of a guidewire may be provided in at least one of the stylets which is inserted into the blood removal lumen and blood feed lumen, running from the engaging part side towards the rear part of the stylet main body.

This means that it is possible to produce a hemodialysis catheter set with which the operation to make the catheter indwelling in the blood vessel of a patient is simplified. Furthermore, there is no need to form a lumen in the catheter for the passage of the guidewire, and therefore the structure of the dialysis catheter which has a blood removal lumen and blood feed lumen can be simplified, and the production of the catheter is also simplified. Furthermore, if a through-hole for the passage of the guidewire is provided in both stylets, it is only necessary to produce one type of stylet.

BRIEF DESCRIPTION OF THE FIGURES

FIG. 2a is a plan view, FIG. 2b is a front view showing the tip end of the catheter of FIG. 2a, and FIG. 2c is a side view;

FIG. 3a is a side view, FIG. 3b is a front view, and FIG. 3c is an enlarged side view showing the tapered tip end part;

FIG. 4a is a side view, FIG. 4b is a front view, and FIG. 4c is an enlarged side view showing the tapered tip end part;

DESCRIPTION OF THE EMBODIMENTS

Figure 1:
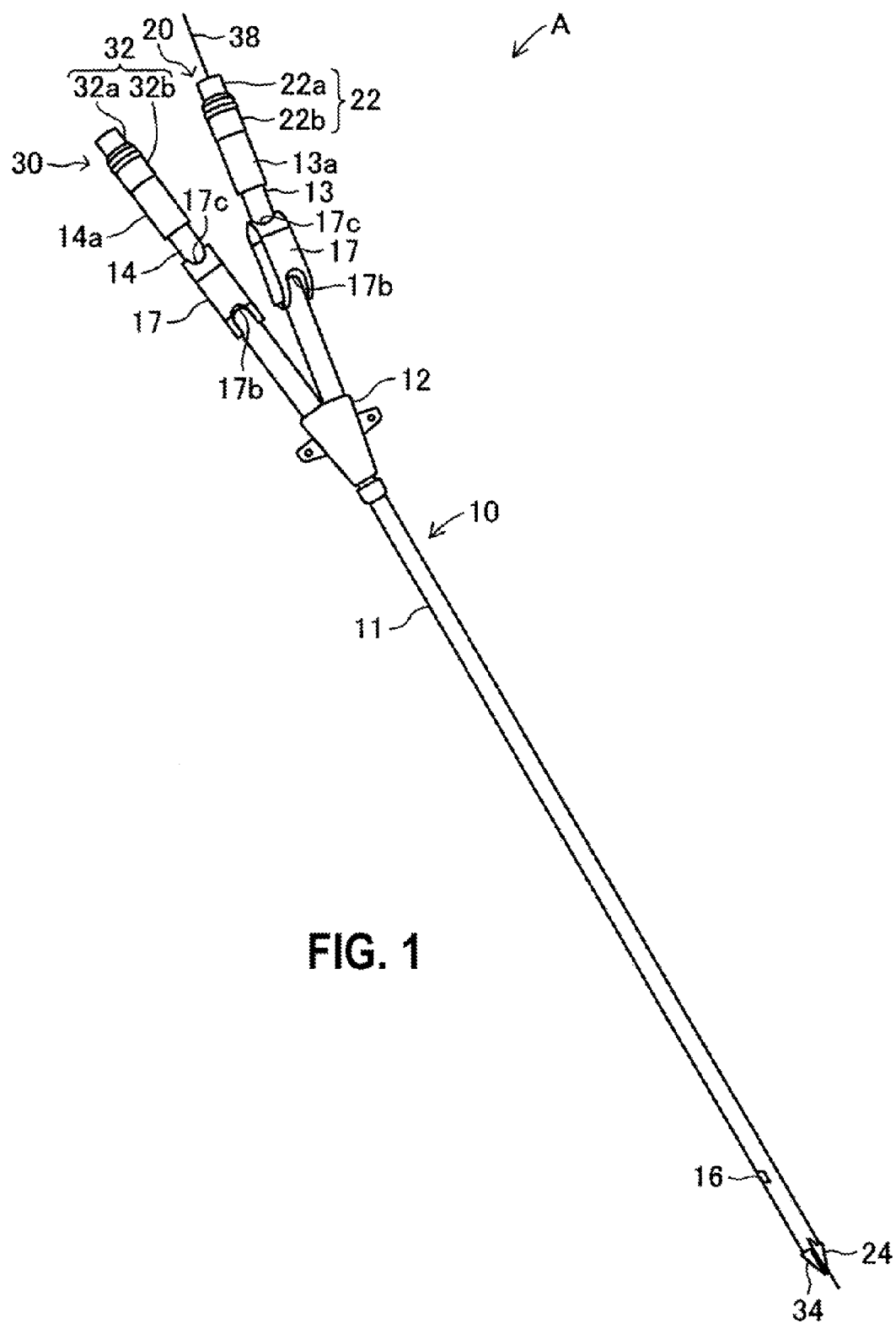
FIG. 1 is a perspective view showing a state in which a guidewire is fitted to a catheter set according to a first embodiment of the present disclosure.
Figure 2A:
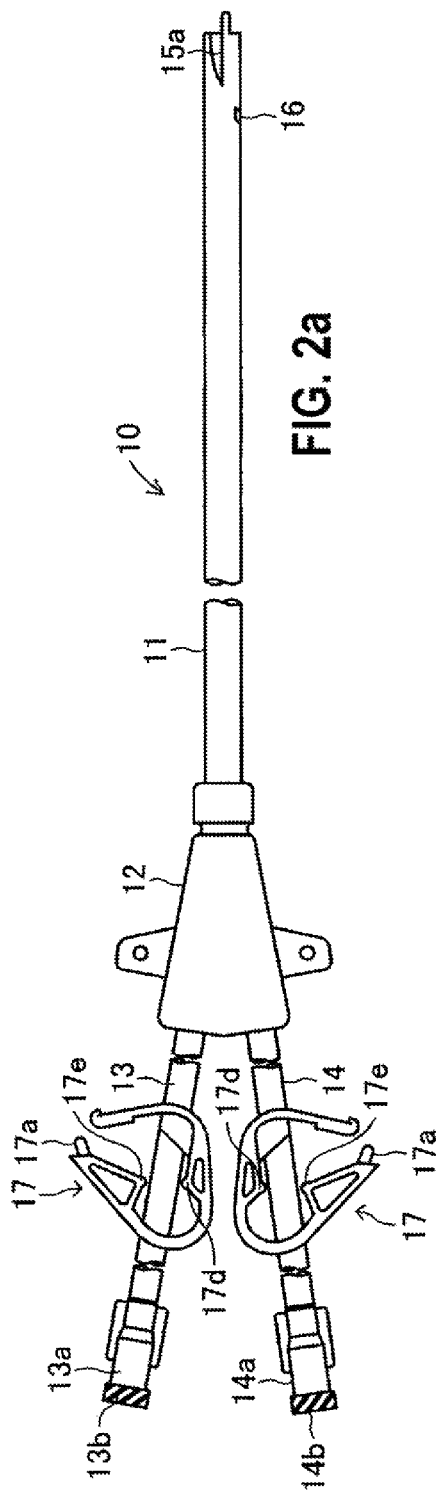
FIGS. 2a-2c show the catheter of the catheter set shown in FIG. 1, where
Figure 2B:
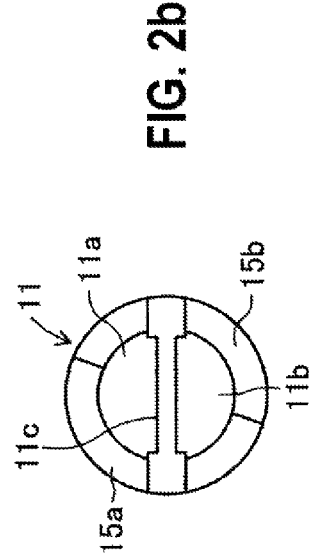
Figure 2C:
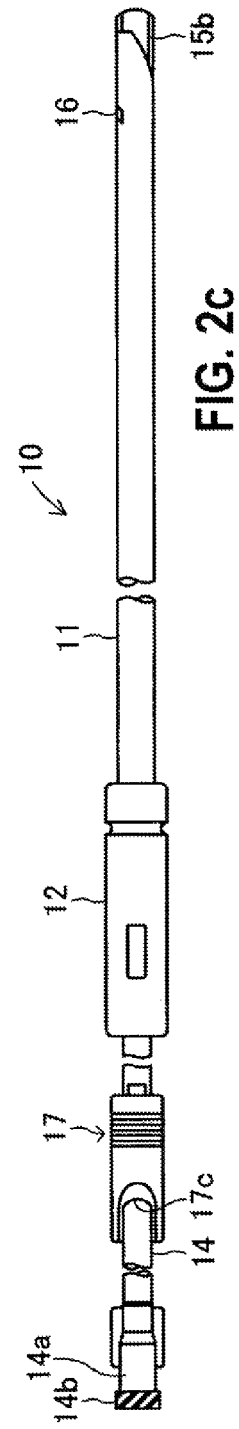

A first embodiment of the present disclosure will be described in detail below with the aid of the FIGS. 1-7. FIG. 1 shows a state in which a guidewire 38 is assembled with a catheter set "A" according to this mode of embodiment. The catheter set A is used for hemodialysis, and it includes: a catheter 10 which is made indwelling within a blood vessel of a patient, and a stylet 20 with a hole (see FIGS. 3a-3c) and a stylet 30 without a hole (see FIGS. 4a-4c) which are respectively inserted into the catheter 10. As shown in FIGS. 2a-2c, the catheter 10 includes an elongate catheter main body 11, and two branch pipes 13, 14 which branch from a connector 12 joined to the base end of the catheter main body 11 (see FIGS. 2a and 2c). The side of the branch pipes 13, 14 in the catheter 10 shall be referred to below as the base end or the rear part, and the opposite side shall be referred to as the tip end or the front part.

The catheter main body 11 includes an elongate flexible cylinder defining a blood removal lumen 11a, a blood feed lumen 11b, and a dividing wall 11c lying between the lumens which divides the inside of the catheter main body 11 in two. Furthermore, a cutaway 15a lying on the blood removal lumen 11a side and a cutaway 15b lying on the blood feed lumen 11b side are formed at the tip end of the catheter main body 11, with a gap of 180° between them around the axis of the catheter main body 11. The cutaway 15a includes a recess having a substantially V-shaped edge which extends in a straight line from the tip end of a first end in the width direction of the dividing wall 11c (the part at the left-hand end of FIG. 2b) towards the base end in the longitudinal direction of the dividing wall 11c, after which it extends obliquely towards the tip end of a second end in the width direction of the dividing wall 11c (the part at the right-hand end of FIG. 2b).

The oblique edge of the cutaway 15a is cut away so as to lie perpendicular to the axis of the catheter main body 11 at the tip end of the second end of the dividing wall 11c, and is joined to the second end of the dividing wall 11c. Furthermore, the cutaway 15b includes a recess having a substantially V-shaped edge which extends in a straight line from the tip end of the second end in the width direction of the dividing wall 11c (the part at the right-hand end in FIG. 2b) towards the base end in the longitudinal direction of the dividing wall 11c, after which it extends obliquely towards the tip end of the first end in the width direction of the dividing wall 11c. The oblique edge of the cutaway 15b is cut away so as to lie perpendicular to the axis of the catheter main body 11 at the tip end of the first end of the dividing wall 11c, and is joined to the first end of the dividing wall 11c.

That is to say, the cutaway 15b is formed so as to overlie the cutaway 15a through a turn of 180° about the axis of the catheter main body 11. Furthermore, the tip end of the dividing wall 11c projects slightly outside of the tip end opening of the catheter main body 11. In this way, the tip end of the dividing wall 11c projects from the tip end of the catheter main body 11, whereby blood which is delivered from the blood feed lumen 11b is prevented from going straight into the blood removal lumen 11a. Furthermore, a pair of rhomboid side holes 16 (only one is shown in the figures) are formed with a gap of 180° between them around the axis of the catheter main body 11 further towards the base end of the catheter main body 11 than the cutaways 15a, 15b. A lumen which communicates with the blood removal lumen 11a and a lumen which communicates with the blood feed lumen 11b are then formed inside the connector 12.

The branch pipe 13 includes a cylinder having a lumen which communicates with the blood removal lumen 11a via one of the lumina of the connector 12, and a luer adapter 13a is joined to the base end of the branch pipe 13. Furthermore, the branch pipe 14 includes a cylinder having a lumen which communicates with the blood feed lumen 11b via the other lumen of the connector 12, and a luer adapter 14a is joined to the base end of the branch pipe 14. A thread 13b is formed on the outer periphery of the open end of the luer adapter 13a, and a thread 14b is formed on the outer periphery of the open end of the luer adapter 14a. Note that the catheter main body 11 and the branch pipes 13, 14 are made of a soft synthetic resin material, such as silicone or polyurethane, and the connector 12 and luer adapters 13a, 14a are made of a synthetic resin material such as polypropylene, polyurethane, polycarbonate or polyacetal.

Furthermore, a clamp 17 for closing off each of the branch pipes 13, 14 is fitted to the branch pipes 13, 14. The clamp 17 is an elongate plate-like element which has been bent to form a substantially triangular elastic frame shape. An engaging recess (not depicted) includes a step formed on the inner surface of one of the end portions of the claim 17, and an engaging protrusion 17a which can engage with the engaging recess is formed at the other end. Furthermore, holes 17b, 17c, which allow for the passage of the branch pipes 13, 14, respectively, are formed at the front and rear of the clamp 17, and the branch pipes 13, 14 pass through the holes 17b, 17c so that the clamp 17 is fitted to the branch pipes 13, 14, respectively.

In addition, pushing parts 17d, 17e for pushing the branch pipes 13, 14 from both sides to close off the lumina thereof when the engaging protrusion 17a has engaged with the engaging recess are formed on opposing portions of the inner peripheral surface of the clamp 17. Accordingly, the engaging protrusion 17a is made to engage with the engaging recess to close off the branch pipes 13, 14, and release of the engagement of the engaging protrusion 17a and the engaging recess allows communication between both ends of the branch pipes 13, 14. The clamp 17 is made of a synthetic resin material such as polypropylene or ABS.

Figure 3A:
FIGS. 3a-3c show the stylet with a hole, where
Figure 3B:
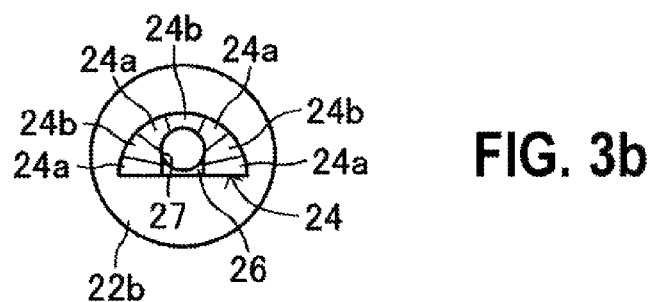
Figure 3C:
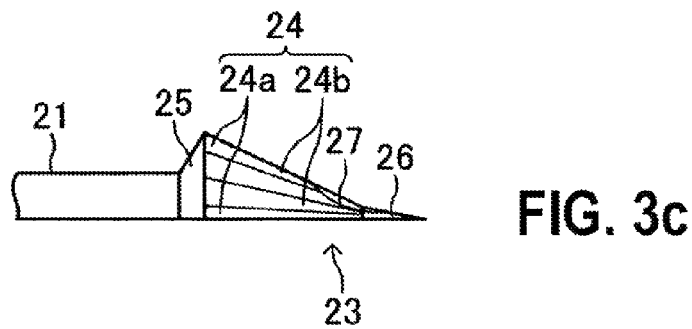

As shown in FIGS. 3a-3c, the stylet 20 with a hole includes a stylet main body 21, a gripping part 22 which is provided at the base end of the stylet main body 21, and a tapered tip end part 23 which is linked to the tip end of the stylet main body 21. The stylet main body 21 includes an elongate cylindrical linear member made of a synthetic resin which can pass through the blood removal lumen 11a and blood feed lumen 11b of the catheter 10. The peripheral edge of the stylet main body 21 has a semicircular shape in cross-section. Furthermore, as shown in FIG. 3c, the tapered tip end part 23 includes an engaging part 24, a film-like linking part 25 which links the rear end of the engaging part 24 to the tip end of the stylet main body 21, and a soft tip end part 26 which is linked to the tip end of the engaging part 24.

The engaging part 24 includes a tapered cylindrical body which has a semicircular shape wherein the cross-section of the rear end is greater than the cross-section of the stylet main body 21, and a semicircular shape wherein the cross-section of the tip end is smaller than the cross-section of the stylet main body 21. Furthermore, the engaging part 24 has soft parts 24a and rigid parts 24b which extend in the front to rear direction, respectively, alternately arranged in the peripheral direction. The flat part (the bottom in FIG. 3c) and the left and right sections on both sides of the bottom (the left and right in the state shown in FIG. 3b) include the soft parts 24a, while the sections next to these soft parts 24a on both sides and the central section of the arc include the rigid parts 24b. Soft parts 24a are then arranged between the rigid part 24b at the center of the arc and the rigid parts 24b on both sides. The engaging part 24 normally maintains a state of radial expansion if the soft parts 24a are kept in a flat state, but it contracts if the rear ends of the rigid parts 24b are urged rearwards in the axial direction of the stylet main body.

The film-like linking part 25 includes a soft, annular film body of semicircular cross-section, in which the rear end is linked to the peripheral edge at the tip end of the stylet main body 21, and the tip end is linked to the peripheral edge at the rear end of the engaging part 24. This film-like linking part 25 freely deforms when force is applied thereto. The rear end of the soft tip end part 26 is linked to the peripheral edge at the tip end of the engaging part 24, and the soft tip end part steadily grows narrower from the rear end towards the tip end. The soft tip end part 26 is provided in order to facilitate deformation of the engaging part 24. Furthermore, as shown in FIG. 3b, a through-hole 27 for the passage of the guidewire 38 is formed in a section from the tip end of the engaging part 24 to the soft tip end part 26. Moreover, the rigid parts 24b of the engaging part 24 may be made of nylon, polyolefin, polycarbonate, ABS resin, or similar, and the soft parts 24a of the engaging part 24, the film-like linking part 25 and the soft tip end part 26 may be made of polyether block amide, polybutadiene, styrene-ethylene-butylene-styrene block copolymer, styrene-butadiene copolymer, or similar.

Furthermore, the gripping part 22 includes a gripping part main body 22a which is joined to the base end of the stylet main body 21, and a cylindrical thread part 22b which is fitted to the gripping part main body 22a in such a way that it can rotate in the axial direction at the outer periphery of the linking part of the gripping part main body 22a with the stylet main body 21. The gripping part main body 22a is formed as a cylindrical shape which has a through-hole (not depicted) which communicates with the through-hole 27 of the stylet main body 21, and the guidewire 38 can pass from this through-hole to the through-hole 27. Furthermore, a thread (not depicted) which can screw together with the thread 13b of the luer adapter 13a and with the thread 14b of the luer adapter 14a is formed on the inner peripheral surface of the cylindrical thread part 22b.

With this stylet 20 with a hole, the stylet main body 21 can be inserted into the blood removal lumen 11a or blood feed lumen 11b of the catheter, in a state in which the tip end tapered part 23 has passed through the inside from the base end of the blood removal lumen 11a or blood feed lumen 11b and projects outwards. Here, the tapered tip end part 23 passes through the inside of the blood removal lumen 11a or blood feed lumen 11b in a compressed state. When the tapered tip end part 23 has projected outside, it returns to its original state of expansion, and the rear ends of the rigid parts 24b of the engaging part 24 engage with the opening edge of the blood removal lumen 11a or blood feed lumen 11b. Furthermore, in this state, the thread of the cylindrical thread part 22b is screwed together with the thread 13b or the thread 14b, whereby the stylet 20 with a hole can be fixed to the catheter 10.

Figure 4A:
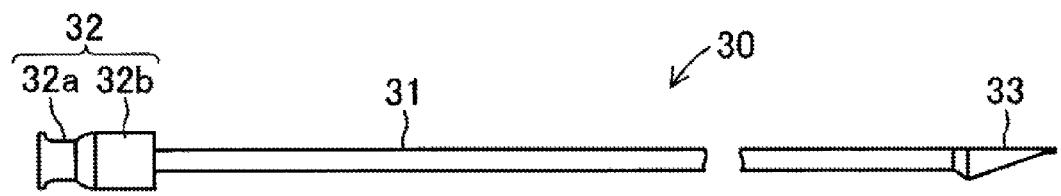
FIGS. 4a-4c show the stylet without a hole, where
Figure 4B:
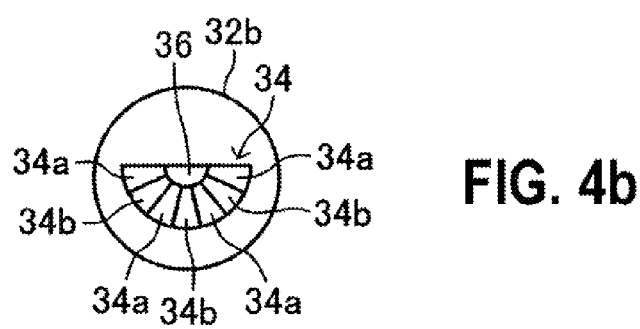
Figure 4C:
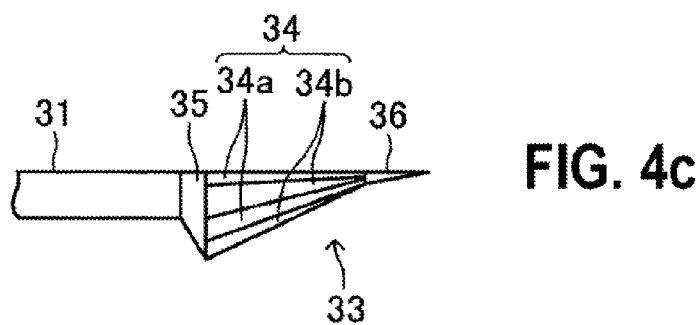

As shown in FIGS. 4a-4c, the stylet 30 without a hole includes a stylet main body 31, a gripping part 32 which is provided at the base end of the stylet main body 31, and a tapered tip end part 33 which is linked to the tip end of the stylet main body 31. The stylet main body 31 includes an elongate cylindrical linear member made of a synthetic resin which can pass through the blood removal lumen 11a and blood feed lumen 11b of the catheter 10. The peripheral edge of the stylet main body 31 has a semicircular shape in cross-section. Furthermore, the tapered tip end part 33 includes an engaging part 34, a film-like linking part 35 which links the peripheral edge of the rear end of the engaging part 34 to the peripheral edge of the tip end of the stylet main body 31, and a soft tip end part 36 which is linked to the tip end of the engaging part 34. The engaging part 34, the film-like linking part 35 and the tapered tip end part 33 including the soft tip end part 36 have the same structure as the tapered tip end part 23 described above, apart from the lack of the through-hole 27.

Furthermore, the gripping part 32 includes a gripping part main body 32a which is joined to the stylet main body 31, and a cylindrical thread part 32b which is fitted to the gripping part main body 32a in such a way that it can rotate in the axial direction at the outer periphery of the linking part of the gripping part main body 32a with the stylet main body 31. A thread (not depicted) which can screw together with the thread 13b of the luer adapter 13a and with the thread 14b of the luer adapter 14a is formed on the inner peripheral surface of the cylindrical thread part 32b. Consequently, the stylet main body 31 is inserted into the blood removal lumen 11a or blood feed lumen 11b, and the thread of the cylindrical thread part 32b is screwed together with the thread 13b or thread 14b, whereby the stylet 30 without a hole can be fixed to the catheter 10. Furthermore, when the tapered tip end parts 23, 33 of the stylet main body 21 and stylet main body 31 are projecting from the tip end of the blood removal lumen 11a or blood feed lumen 11b, respectively, the tip end shape which is formed by the two is substantially conical.

The guidewire 38 is inserted beforehand into a prescribed area inside the blood vessel of the patient and used to guide the catheter 10. The guidewire 38 is made of stainless steel of which the outer diameter is 0.5-1.0 mm. Moreover, when the guidewire 38 is inserted into the blood vessel, a cannula (not depicted) including a cylindrical puncture needle is used to pierce the patient's body, and the tip end thereof is made to reach the blood vessel. Next, the guidewire 38 is passed through the cannula, and the tip end of the guidewire 38 is inserted into the blood vessel. Then the cannula is withdrawn from the patient's body with the guidewire 38 remaining in the patient's body, and the catheter 10 is made indwelling using the guidewire 38, in an operation that will be described later.

When catheter set A configured in this manner is produced, the stylet 20 with a hole and stylet 30 without a hole are first assembled with the catheter 10, and then the assembled catheter set A undergoes a sterilization treatment. Hemodialysis is then carried out using the sterilized catheter set A. In this case, as shown in FIG. 2a, the stylet 20 with a hole is inserted from the tapered tip end part 23 side into the opening of the luer adapter 13a of the branch pipe 13, for example, of the catheter 10 to which the clamp 17 has been fitted loosely around the branch pipes 13, 14, respectively. Insertion continues towards the tip end opening of the blood removal lumen 11a of the catheter main body 11.

In this case, the tapered tip end part 23 passes through the blood removal lumen 11a in a state in which it is restricted by the inner surface of the blood removal lumen 11a so as to become compressed and narrow. Then, when the tapered tip end part 23 projects outside from the tip end opening of the catheter main body 11, the restriction imparted by the blood removal lumen 11a is released, and the tapered tip end part 23 expands in the radial direction, and the rear ends of the rigid parts 24b of the engaging part 24 engage with the opening edge of the blood removal lumen 11a. Next, the thread of the cylindrical thread part 22b is screwed together with the thread 13b, whereby the stylet 20 with a hole is fixed to the catheter 10. By means of this, the stylet 20 with a hole can no longer move with respect to the catheter 10, and the fitting of the stylet 20 with a hole into the blood removal lumen 11a of the catheter 10 is complete.

Next, the stylet 30 without a hole is inserted from the tapered tip end part 33 side into the opening of the luer adapter 14a of the branch pipe 14. Insertion continues towards the tip end opening of the blood feed lumen 11b of the catheter main body 11. In this case too, the tapered tip end part 33 passes through the blood feed lumen 11b in a compressed and narrow state. Then, when the tapered tip end part 33 projects outside from the tip end opening of the catheter main body 11, the tapered tip end part 33 expands in the radial direction, and the rear ends of the rigid parts 34b of the engaging part 34 engage with the opening edge of the blood feed lumen 11b. Next, the thread of the cylindrical thread part 32b is screwed together with the thread 14b, whereby the stylet 30 without a hole is fixed to the catheter 10.

Figure 5:
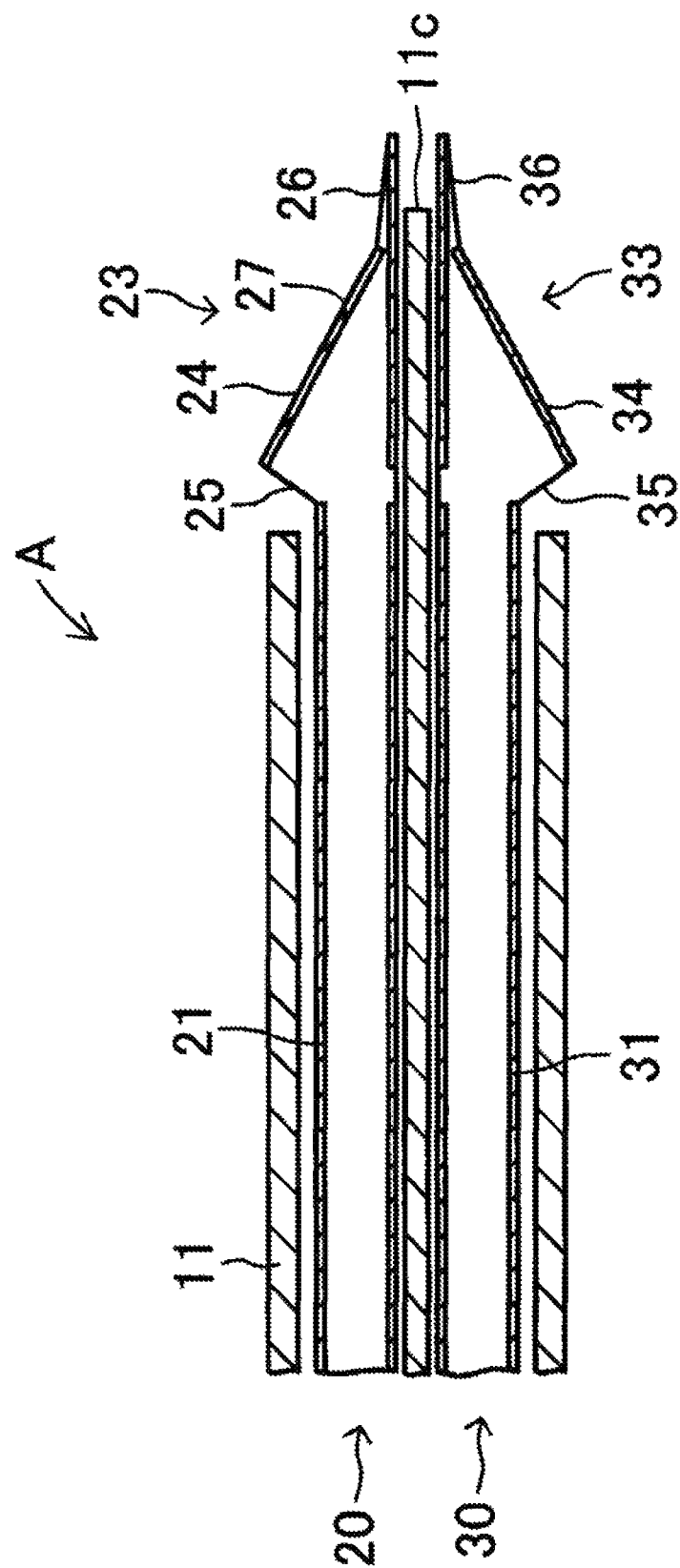
FIG. 5 is a cross-sectional view showing the main parts when the stylet with a hole and stylet without a hole have been assembled with the catheter.

By means of this, the stylet 30 without a hole can no longer move with respect to the catheter 10, and the fitting of the stylet 30 without a hole into the blood feed lumen 11b of the catheter 10 is complete. Here, the projecting section which grows steadily narrower from the tip end opening of the catheter main body 11 towards the front is formed by the tapered tip end part 23 of the stylet 20 with a hole which projects from the tip end opening of the blood removal lumen 11a, and the tapered tip end part 33 of the stylet 30 without a hole which projects from the tip end opening of the blood feed lumen 11b, as shown in FIG. 5. Here, the tapered tip end part 23 and the tapered tip end part 33 are facing each other so as to lie on either side of the tip end of the dividing wall 11c which projects from the tip end of the catheter main body 11.

In this way, the catheter 10 to which the stylet 20 with a hole and the stylet 30 without a hole have been fitted, and which is formed with a tapered projection at the tip end, is made indwelling within a blood vessel using the guidewire 38, of which the tip end has been inserted into the blood vessel as described above. In this case, the rear end of the guidewire 38 which extends from inside the patient's body is inserted into the stylet 20 with a hole from the through-hole 27 in the tapered tip end part 23 of the stylet 20 with a hole, and the rear end is made to project outside of the opening in the gripping part main body 22a.

Figure 6:
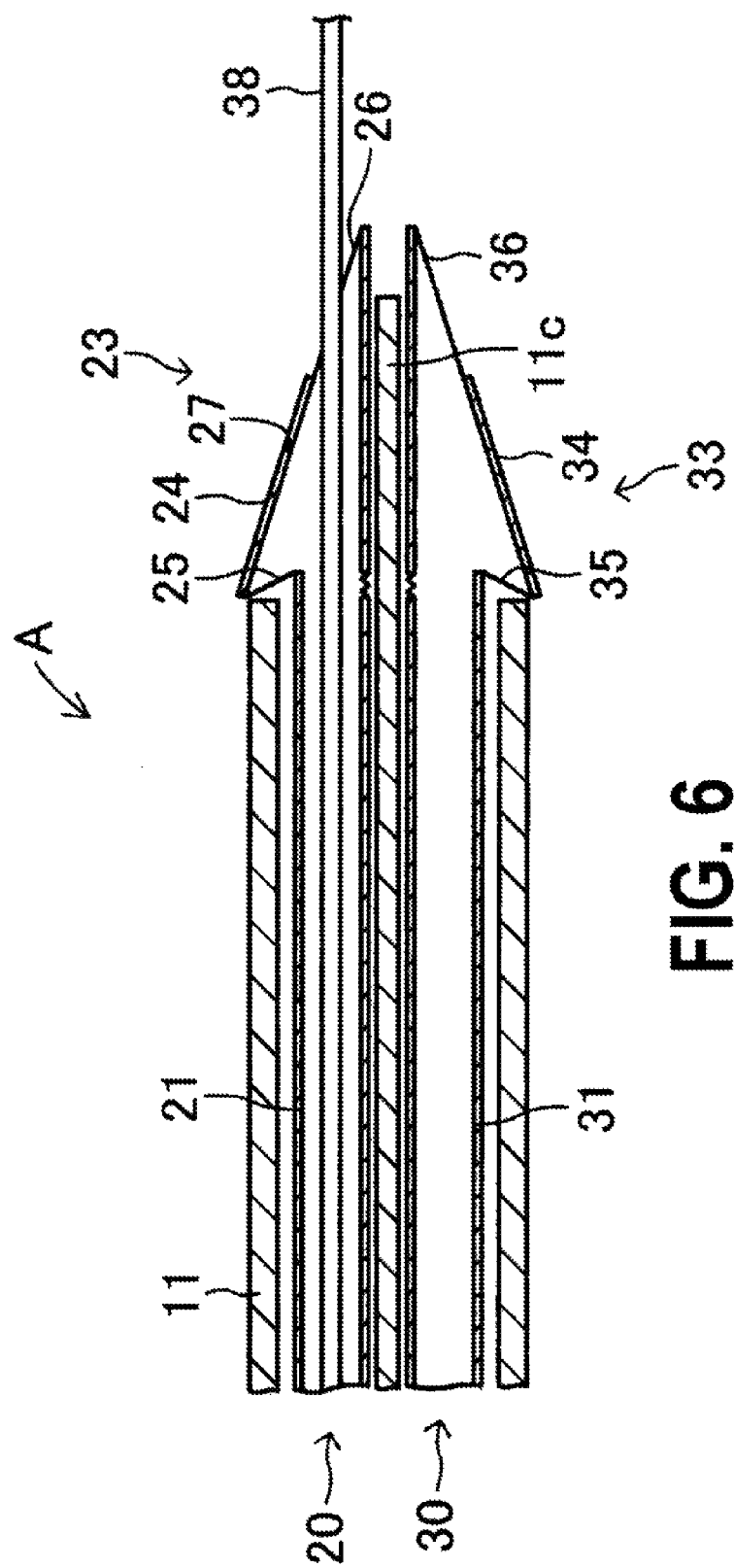
FIG. 6 is a cross-sectional view showing the main parts when the catheter set is inserted within a lumen in a patient's body.

The catheter 10 is then inserted into the patient's body along the guidewire 38 together with the stylet 20 with a hole and stylet 30 without a hole, and the tip end opening of the catheter main body 11 is positioned inside the blood vessel. Here, a rearward force is applied to the tapered tip end parts 23, 33, as shown in FIG. 6, but the sections of the engaging parts 24, 34 on the outer peripheral side at the rear end engage with the respective edges at the tip end opening of the catheter main body 11 so that the tapered tip end parts 23, 33 are prevented from retracting inside the catheter main body 11. Furthermore, the shape of the tapered tip end parts 23, 33 is kept as a shape which grows steadily narrower from the tip end opening of the catheter main body 11 towards the front by means of the engaging parts 24, 34.

Figure 7:
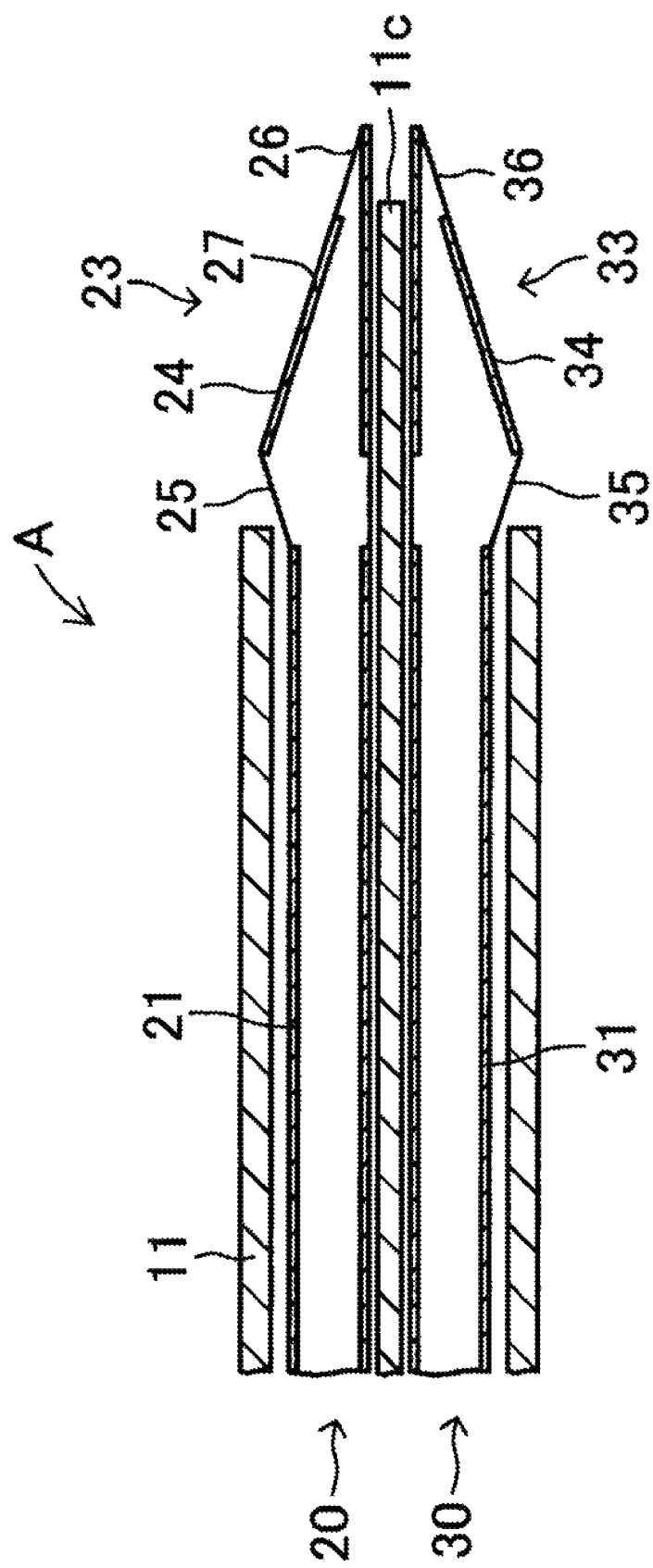
FIG. 7 is a cross-sectional view showing the main parts when the stylet with a hole and stylet without a hole are withdrawn from the catheter.

Next, the guidewire 38, stylet 20 with a hole and stylet 30 without a hole are withdrawn in succession from the catheter 10, whereby only the catheter 10 remains in the patient's body. At this point, the guidewire 38 is withdrawn from the stylet 20 with a hole, after which the thread of the cylindrical thread part 22b and the thread 13b are unscrewed, while the thread of the cylindrical thread part 32b and the thread 14b are also unscrewed. The gripping part 22 of the stylet 20 with a hole and the gripping part 32 of the stylet 30 without a hole are then pulled rearwards. This causes the tapered tip end parts 23, 33 to contract in the radial direction and to retract inside the catheter main body 11, as shown in FIG. 7.

At this point, the gripping parts 22, 32 are pulled rearwards, whereby the film-like linking parts 25, 35 enter the catheter main body 11. Next, the sections at the rear of the engaging parts 24, 34 are pulled rearwards into the catheter main body 11 by means of the film-like linking parts 25, 35. This is designed to flatten the soft parts 24a, 34a of the engaging parts 24, 34 so that the rigid parts 24b, 34b are brought closer together, and the tapered tip end parts 23, 33 are each radially contracted. At this point, the stylet 20 with a hole and the stylet 30 without a hole may be withdrawn at the same time, or they may be withdrawn one at a time in succession.

The blood removal side of a dialysis circuit for sucking out blood is then connected to the luer adapter 13a of the branch pipe 13, and the blood feeding side of the dialysis circuit for returning purified blood to a blood vessel in the body is connected to the luer adapter 14a of the branch pipe 14. A dialysis device which is connected to the dialysis circuit is operated in this state in order to carry out hemodialysis. Here, the blood inside the blood vessel is taken out via the blood removal lumen 11a and purified by the dialysis device, after which the blood is returned to the blood vessel via the blood feed lumen 11b. In this process, some of the blood which has been removed passes through the side hole 16 which is provided on the blood removal lumen 11a side of the catheter main body 11, and some of the blood which is fed passes through the side hole 16 on the blood feed lumen 11b side of the catheter main body 11. Furthermore, the blood which is delivered via the blood feed lumen 11b is prevented from going straight into the blood removal lumen 11a by means of the tip end of the dividing wall 11c which projects from the tip end opening of the catheter main body 11.

In this way, with catheter set A according to this mode of embodiment, the catheter 10 is a double-lumen-type catheter which is provided with the blood removal lumen 11a and the blood feed lumen 11b. The stylet 20 with a hole which allows the passage of the guidewire 38 and the stylet 30 without a hole are used as the stylets. The stylet 20 with a hole and stylet 30 without a hole include long tubular stylet main bodies 21, 31 and tapered tip end parts 23, 33, respectively. Furthermore, the tapered tip end parts 23, 33 have engaging parts 24, 34 in which the soft parts 24a, 34a and rigid parts 24b, 34b are alternately arranged, the soft film-like linking parts 25, 35 for linking the stylet main bodies 21, 31 and engaging parts 24, 34, and soft tip end parts 26, 36 which are formed at the tip end of the engaging parts 24, 34.

Then, when the stylet 20 with a hole and the stylet 30 without a hole have been assembled with the catheter 10, the tip end opening of the catheter main body 11 is closed off by means of the tapered tip end parts 23, 33, and a projection having a curved surface which grows steadily narrower in diameter from the tip end of the catheter main body 11 towards the front is formed at the tip end of the catheter main body 11 by the tapered tip end parts 23, 33. Consequently, the insertion resistance of the catheter 10 is reduced and the handling is improved. Furthermore, when the stylet 20 with a hole and stylet 30 without a hole are withdrawn from the catheter 10, the stylet 20 with a hole and stylet 30 without a hole are pulled towards the base end so that they can be easily withdrawn.

Furthermore, the engaging parts 24, 34 are designed with soft parts 24a, 34a and rigid parts 24b, 34b arranged alternately in the peripheral direction, and therefore the soft parts 24a, 34a are flattened so that the rigid parts 24b, 34b are brought closer together when the stylet 20 with a hole and the stylet 30 without a hole are pulled, and the whole of the engaging parts 24, 34 is reliably contracted. In addition, when the force which urges the rear ends of the engaging parts 24, 34 towards the radial center is released, the rear parts of the engaging parts 24, 34 are urged so as to radially expand, and if the tapered tip end parts 23, 33 are pressed rearwards in this state, the rear ends of the engaging parts 24, 34 reliably engage with the edges at the tip end opening of the catheter main body 11. This makes it possible to prevent the tapered tip end parts 23, 33 from retracting inside the catheter main body 11.

Furthermore, the soft tip end parts 26, 36 are provided at the tip ends of the engaging parts 24, 34, and therefore the sections at the rear of the engaging parts 24, 34 readily deform with the soft tip end parts 26, 36 at the center when the rear parts of the engaging parts 24, 34 are radially contracted or expanded. In addition, the stylet 20 with a hole and stylet 30 without a hole are used as the stylets, and therefore the strength of the catheter 10 is increased, which simplifies the insertion operation. Furthermore, the tip end of the dividing wall 11c which projects from the tip end of the catheter main body 11 is designed to lie between the tapered tip end parts 23, 33, and therefore the tip end of the dividing wall 11c can be protected. In addition, the guidewire 38 is utilized, and therefore the operation to make the catheter 10 indwelling within the patient's blood vessel is simplified. Furthermore, the stylet 20 with a hole is provided with the through-hole 27, which means that there is no need to form a lumen for the passage of the guidewire 38 in the catheter 10, and therefore the structure of the catheter 10 can be simplified and the catheter 10 can be produced more easily.

Figure 8:
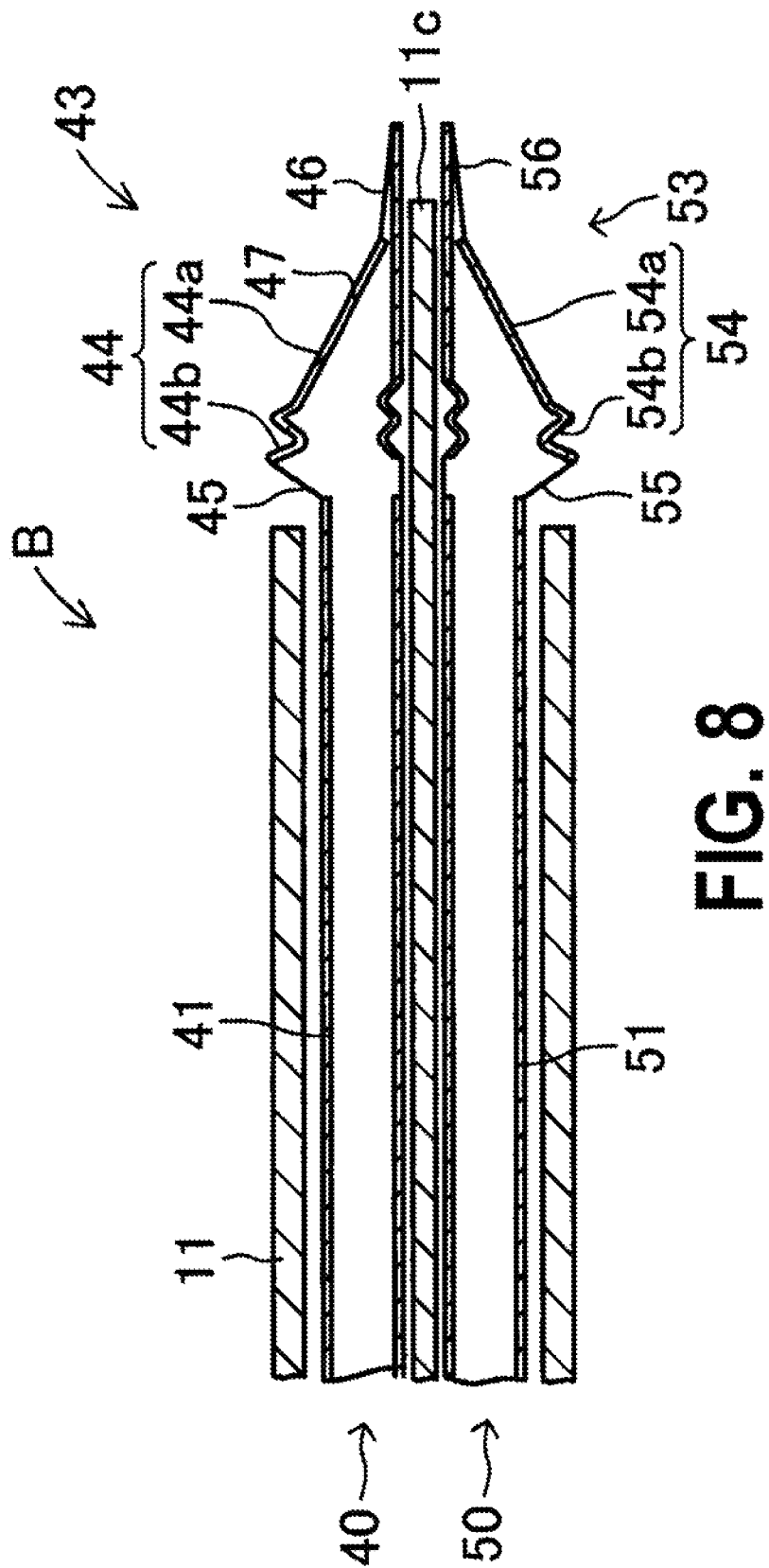
FIG. 8 is a cross-sectional view showing the main parts when the stylet with a hole and stylet without a hole have been assembled with the catheter according to a second embodiment of the present disclosure.
Figure 9:
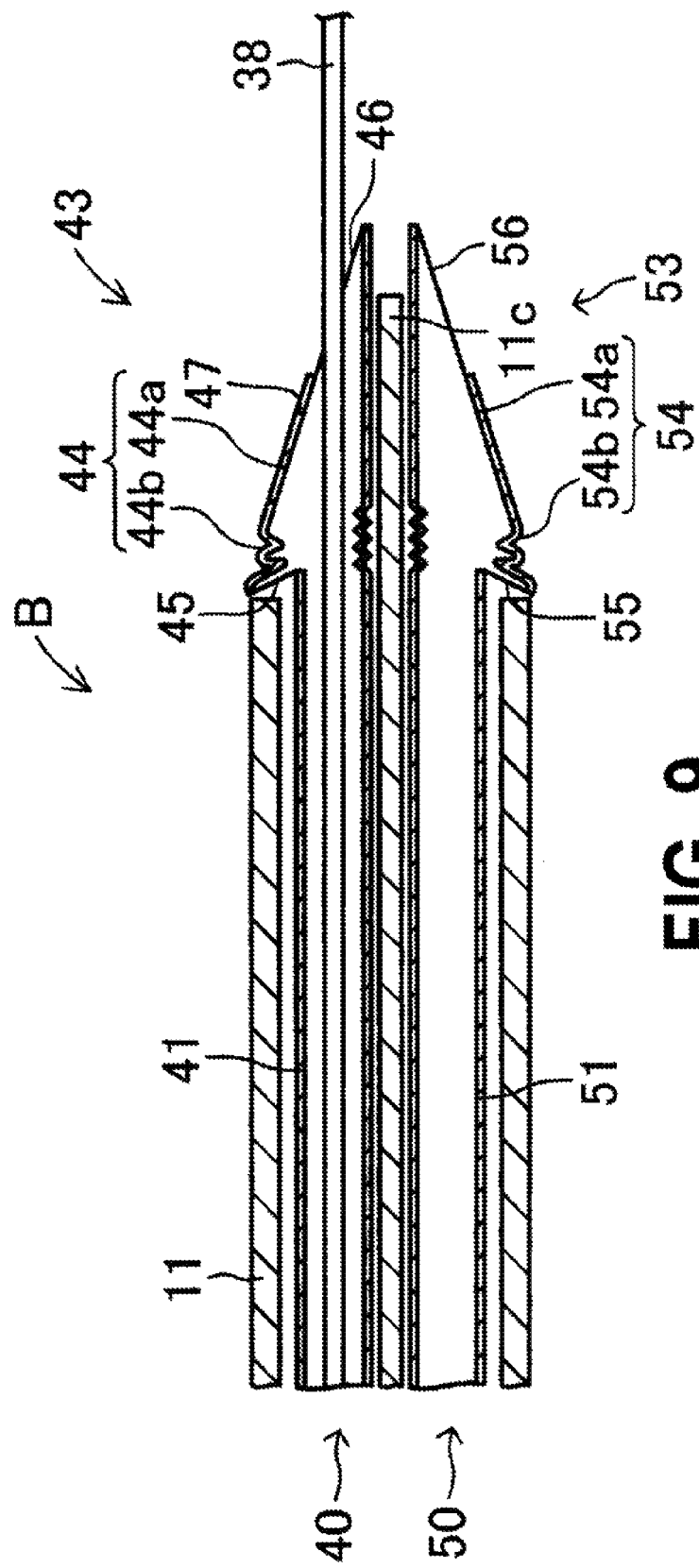
FIG. 9 is a cross-sectional view showing the main parts when the catheter set shown in FIG. 8 is inserted within a lumen in a patient's body.
Figure 10:
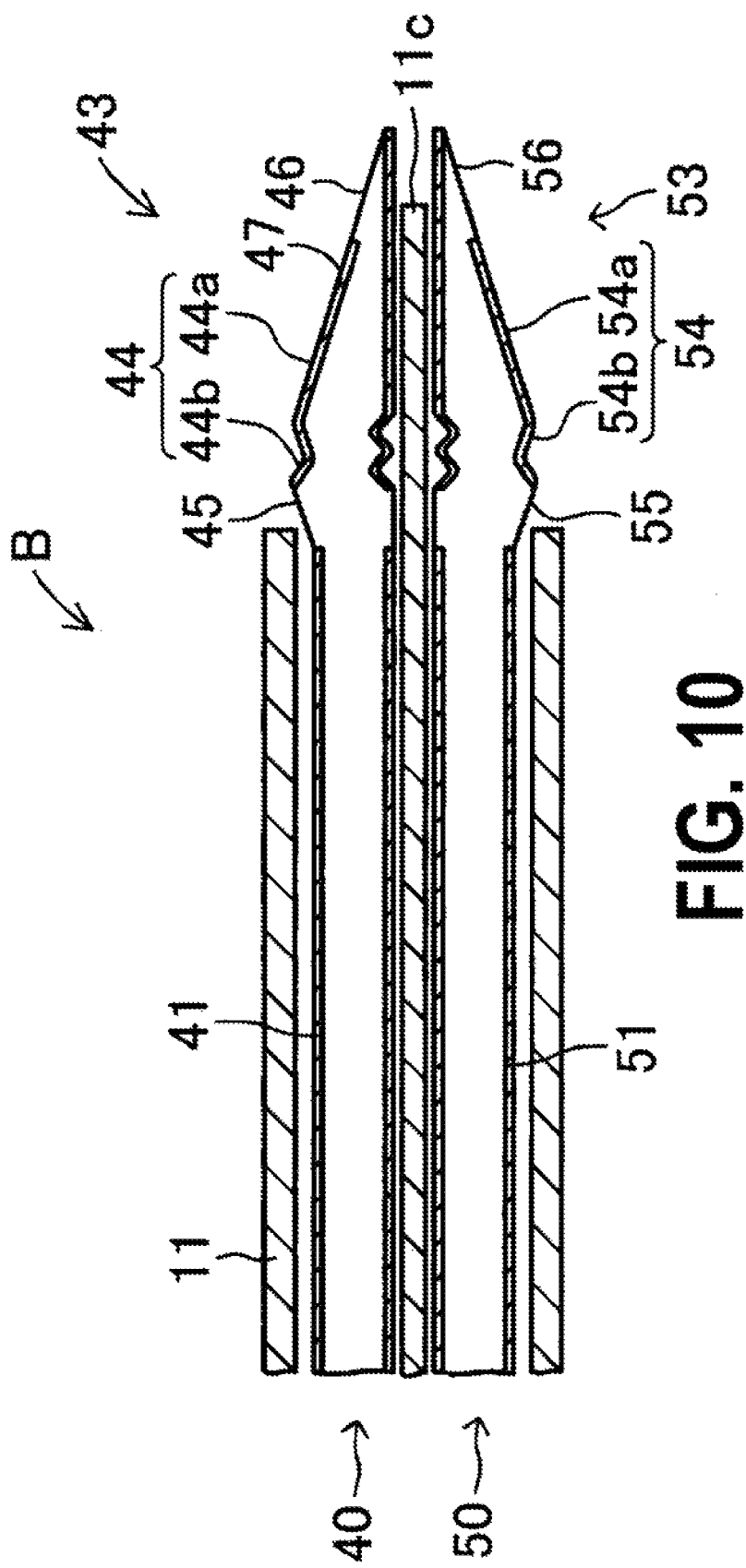
FIG. 10 is a cross-sectional view showing the main parts when the stylet with a hole and stylet without a hole are withdrawn from the catheter shown in FIG. 8.

FIGS. 8 to 10 show the main parts of a catheter set "B" according to a second embodiment of the present disclosure. With this catheter set B, a tapered tip end part 43 of a stylet with a hole 40 includes an engaging part 44, a film-like linking part 45 which links the peripheral edge at the rear end of the engaging part 44 to the peripheral edge at the tip end of a stylet main body 41, and a soft tip end part 46 which is linked to the tip end of the engaging part 44. The engaging part 44 has a structure in which a bellows-like expandable part 44b is connected to the rear part of a tapered rigid cylindrical body 44a which has a semicircular shape wherein the cross-sectional shape of the rear end is substantially the same size as the cross-section of the stylet main body 41, and a semicircular shape wherein the cross-sectional shape of the tip end is smaller than the cross-section of the stylet main body 41.

The engaging part 44 normally maintains a state of radial expansion if the expandable part 44b is kept at a prescribed length, as shown in FIG. 8, but the outer diameter thereof increases and the expandable part 44b contracts if it is compressed in the axial direction, as shown in FIG. 9, and the expandable part 44b extends and the outer diameter thereof decreases if it is pulled lengthwise in the axial direction. A through-hole 47 for the passage of the guidewire 38 is then formed in a section from the tip end of the rigid cylindrical body 44a to the soft tip end part 46. Note that the film-like linking part 45 has the same structure as the film-like linking part 25 described above, and the soft tip end part 46 has the same structure as the soft tip end part 26 described above.

Furthermore, a tapered tip end part 53 of a stylet 50 without a hole includes an engaging part 54, a film-like linking part 55 which links the peripheral edge at the rear end of the engaging part 54 to the peripheral edge at the tip end of a stylet main body 51, and a soft tip end part 56 which is linked to the tip end of the engaging part 54. The engaging part 54 has a structure in which a bellows-like expandable part 54b is connected to the rear part of a tapered rigid cylindrical body 54a which has a semicircular shape wherein the cross-sectional shape of the rear end is substantially the same size as the cross-section of the stylet main body 51, and a semicircular shape wherein the cross-sectional shape of the tip end is smaller than the cross-section of the stylet main body 51.

The engaging part 54 normally maintains a state of radial expansion if the expandable part 54b is kept at a prescribed length, as shown in FIG. 8, but the outer diameter thereof increases and the expandable part 54b contracts if it is compressed in the axial direction, as shown in FIG. 9, and the expandable part 54b extends and the outer diameter thereof decreases if it is pulled lengthwise in the axial direction. Furthermore, the film-like linking part 55 has the same structure as the film-like linking part 35 described above, and the soft tip end part 56 has the same structure as the soft tip end part 36 described above. Moreover, the sections of the expandable parts 44b, 54b on the dividing wall 11c side project towards the inside of the expandable parts 44b, 54b when the expandable parts 44b, 54b are contracted, and they are formed so as not to project outwards. The structures of the other components of the catheter set B are the same as those of the catheter set A described above.

The stylet 40 with a hole configured in the manner described above is inserted into the blood removal lumen 11a of the catheter main body 11, for example, and the stylet 50 without a hole is inserted into the blood feed lumen 11b of the catheter main body 11. In this case, the stylet 40 with a hole and the stylet 50 without a hole pass through the inside of the catheter main body 11 in a state in which the expandable parts 44b, 54b are extended so that the tapered tip ends 43, 53 are narrower. Then, when the tapered tip ends 43, 53 project outside of the tip end opening of the catheter main body 11, the expandable parts 44b, 54b return to their original state and expand in the radial direction.

Furthermore, the catheter 10 is then inserted into the patient's body along the guidewire 38 together with the stylet 40 with a hole and stylet 50 without a hole, and when the tip end opening of the catheter main body 11 is positioned inside the blood vessel, a rearward force is applied to the tapered tip end parts 43, 53, as shown in FIG. 9. At this point, the expandable parts 44b, 54b contract, and the outer peripheral sections of the expandable parts 44b, 54b expand in the radial direction. By means of this, the expandable parts 44b, 54b engage with the respective edges at the tip end opening of the catheter main body 11, and the tapered tip end parts 43, 53 are prevented from retracting inside the catheter main body 11. Here, the shape of the tapered tip end parts 43, 53 is kept as a shape which grows steadily narrower from the tip end opening of the catheter main body 11 towards the front by means of the rigid cylindrical bodies 44a, 54a.

Furthermore, when the stylet 40 with a hole and the stylet 50 without a hole are withdrawn from the catheter main body 11, the gripping part (not depicted) of the stylet 40 with a hole and the gripping part (not depicted) of the stylet 50 without a hole are pulled rearwards. By means of this, the tapered tip ends 43, 53 are restricted by the inner surface of the catheter main body 11 so that they contract, and they retract inside the catheter main body 11, as shown in FIG. 10. At this point, the gripping parts are pulled rearwards, whereby the film-like linking parts 45, 55 respectively enter the catheter main body 11. Next, the engaging parts 44, 54 are pulled rearwards into the catheter main body 11 by means of the film-like linking parts 45, 55, and the expandable parts 44b, 54b extend and become narrower. In this case too, the stylet 40 with a hole and the stylet 50 without a hole may be withdrawn at the same time, or they may be withdrawn one at a time in succession.

In this way, with catheter set B according to this mode of embodiment, the engaging parts 44, 54 include the rigid cylindrical bodies 44a, 54a, and the bellows-like expandable parts 44b, 54b, and therefore when the catheter 10 is inserted into the body, the expandable parts 44b, 54b contract, whereby the outer diameter thereof increases, and the engaging parts engage with the edge at the tip end opening of the catheter main body 11. Furthermore, when the stylet 40 with a hole and the stylet 50 without a hole are withdrawn from the catheter 10, the expandable parts 44b, 54b extend whereby the outer diameter thereof decreases, and the stylet 40 with a hole and stylet 50 without a hole can be easily withdrawn from the catheter 10. The other operational effects of the catheter set B are those as those of the catheter set A described above.

The catheter set according to the present disclosure is not limited to the modes of embodiment described above, and suitable modifications may be made. For example, the stylet main bodies 31, 51 of the stylets 30, 50 without a hole are cylindrical in the modes of embodiment described above, but the stylet main bodies 31, 51 may include solid rod-like bodies. Furthermore, the stylet main bodies of the stylets 20, 40 with a hole may be formed as cylinders having a through-hole corresponding to the diameter of the guidewire 38. In addition, the stylets 20, 40 with a hole are inserted into the blood removal lumen 11a, while the stylets 30, 50 without a hole are inserted into the blood feed lumen 11b in the modes of embodiment described above, but the stylets 30, 50 without a hole may be inserted into the blood removal lumen 11a, and the stylets 20, 40 with a hole may be inserted into the blood feed lumen 11b.

Furthermore, it is possible to dispense with either the stylets 20, 40 with a hole or the stylets 30, 50 without a hole. If the stylets 20, 40 with a hole are dispensed with, the guidewire 38 is not used. In addition, the stylets 20, 40 with a hole may be combined, or the stylets 30, 50 without a hole may be combined as the pair of stylets. Furthermore, the catheter is not limited to the catheter 10 described above, and various shapes of catheter may be used. For example, it is possible to use a cylindrical catheter with a single lumen as the catheter. In this case, the stylet used has a cylindrical or columnar stylet main body and a conical tapered tip end part.

What is claimed is:

1. A stylet which is inserted into a lumen of a catheter, the stylet comprising:
    first and second stylets, each stylet including:
    a stylet main body;
    a tapered tubular engaging part of which a rear end engages an edge at a tip end opening of the catheter by pressing the engaging part towards a base end of the catheter in a state in which the shape of a tip end part is substantially maintained and a rear part is urged so as to expand in a radial direction and project from the tip end opening of the catheter such that when the two stylets have been inserted into the lumens of the catheter, the engaging parts of the two stylets projecting from the tip end opening of the catheter form a substantially conical shape; and
    a soft linking part which links a tip end of the stylet main body and the rear end of the engaging part;
    whereby when the stylet main body is pulled towards the base end of the catheter, from a state in which the stylet main body is inserted into the lumen of the catheter and the engaging part is projecting from the tip end opening of the catheter, the rear part of the engaging part contracts in the radial direction, and the engaging part passes through the lumen of the catheter so that it can be withdrawn at the base end of the catheter.

2. A stylet according to claim 1, wherein the engaging part further comprises rigid parts and soft parts arranged alternately in a peripheral direction in order to allow radial expansion and contraction.

3. A stylet according to claim 1, wherein the rear part of the engaging part is formed as a bellows-like expandable shape in order to allow the engaging part to expand and contract in a radial direction.

4. A stylet according to claim 1, wherein the linking part further comprises an annular film part for linking a peripheral edge at the tip end of the stylet main body and a peripheral edge at the rear end of the engaging part.

5. A stylet according to claim 1, further comprising a through-hole for the passage of a guidewire from the tip end of the engaging part towards the rear end of the stylet main body in at least one of the two stylets.

6. A catheter set in which a catheter includes two lumens which are divided by a dividing wall, and a stylet according to claim 1 wherein each of the first and second stylets can be inserted into one of the two lumens.

* * * * *